United States Patent [19]
Baier et al.

[11] Patent Number: 6,028,027
[45] Date of Patent: Feb. 22, 2000

[54] METHOD OF PRODUCING SELECTIVE-DEHYDROGENATION CATALYSTS, AND CATALYSTS PRODUCED IN THIS WAY

[75] Inventors: Michael Baier, München; Christopher William Rieker, Hassloch; Otto Hofstadt, Altrip; Wolfgang Büchele, Ludwigshafen; Wolfgang Jürgen Pöpel, Darmstadt; Hermann Petersen, Grünstadt; Norbert Neth, Bobenheim-Roxheim, all of Germany

[73] Assignee: BASF Aktiengesellschaft, Ludwigshafen, Germany

[21] Appl. No.: 09/029,643

[22] PCT Filed: Sep. 13, 1996

[86] PCT No.: PCT/EP96/04028

§ 371 Date: Mar. 17, 1998

§ 102(e) Date: Mar. 17, 1998

[87] PCT Pub. No.: WO97/10898

PCT Pub. Date: Mar. 27, 1997

[30] Foreign Application Priority Data

Sep. 23, 1995 [DE] Germany ............... 195 35 416

[51] Int. Cl.⁷ .............. B01J 23/00; B01J 23/58; C07C 15/00; C07C 2/00; C07C 5/333
[52] U.S. Cl. ............ 502/300; 502/328; 502/330; 502/332; 502/338; 502/304; 502/316; 502/319; 502/321; 502/340; 502/355; 585/407; 585/410; 585/411; 585/418; 585/420; 585/421; 585/433; 585/654; 585/659; 585/661; 585/662; 585/663
[58] Field of Search ................. 502/330, 328, 502/332, 338, 304–307, 316, 319, 321, 340–344, 355, 300; 585/407, 410, 411, 418, 420, 421, 433, 654, 659, 661–663

[56] References Cited

U.S. PATENT DOCUMENTS

| | | | |
|---|---|---|---|
| 3,904,552 | 9/1975 | O'Hara | 252/458 |
| 4,052,338 | 10/1977 | Riesser | 252/470 |
| 4,098,723 | 7/1978 | Riesser | 252/474 |
| 4,143,083 | 3/1979 | Reisser | 260/669 |
| 4,144,197 | 3/1979 | Reisser | 252/462 |
| 4,435,607 | 3/1984 | Imai | 585/659 |
| 4,460,706 | 7/1984 | Imanari et al. | 502/344 |
| 4,658,074 | 4/1987 | Bajars et al. | 585/380 |
| 4,684,619 | 8/1987 | Moore | 502/330 |
| 4,749,674 | 6/1988 | Dejaifve et al. | 502/304 |
| 4,758,543 | 7/1988 | Sherrod et al. | 502/174 |
| 4,857,498 | 8/1989 | Dejaifve et al. | 502/304 |
| 4,880,764 | 11/1989 | Imai et al. | 502/330 |
| 4,975,269 | 12/1990 | Watson et al. | 423/594 |
| 4,975,407 | 12/1990 | Dejaifve et al. | 502/330 |
| 5,017,543 | 5/1991 | De Clippeleir et al. | 502/330 |
| 5,190,906 | 3/1993 | Murakami et al. | 502/304 |
| 5,258,348 | 11/1993 | Van Buren et al. | 502/330 |
| 5,376,613 | 12/1994 | Dellinger et al. | 502/304 |
| 5,510,552 | 4/1996 | Dellinger et al. | 585/444 |
| 5,559,066 | 9/1996 | Poepel et al. | 502/20 |
| 5,824,831 | 10/1998 | Shiraki et al. | 502/330 |

FOREIGN PATENT DOCUMENTS

| | | |
|---|---|---|
| 177832 | 4/1986 | European Pat. Off. |
| 1881999 | 5/1986 | European Pat. Off. |
| 195252 | 9/1986 | European Pat. Off. |

*Primary Examiner*—Mark L. Bell
*Assistant Examiner*—Patricia L. Hailey
*Attorney, Agent, or Firm*—Keil & Weinkauf

[57] ABSTRACT

Catalysts comprising iron and potassium and, if desired, further elements, which catalysts are suitable for dehydrogenating hydrocarbons to give the corresponding olefinically unsaturated hydrocarbons, are prepared by calcining a finely divided dry or aqueous mixture of an iron compound with a potassium compound and, if desired, compounds of further elements in a first step that agglomerates having a diameter of from 5 to 50 $\mu$m and formed from smaller individual particles are obtained and, in a second step, preferably after shaping, calcining it at from 300 to 1000° C., with the maximum calcination temperature in the second step preferably being at least 30° below the calcination temperature in the first step. The catalysts thus prepared are useful, in particular, for dehydrogenating ethylbenzene to give styrene.

16 Claims, No Drawings

METHOD OF PRODUCING SELECTIVE-DEHYDROGENATION CATALYSTS, AND CATALYSTS PRODUCED IN THIS WAY

This is the U.S. national stage of PCT international application PCT/EP96/04028, and is filed under 35 U.S.C. 371.

The invention relates to an improved process for preparing catalysts comprising iron and potassium and preferably cerium and, if desired, further elements, which catalysts are suitable for dehydrogenating hydrocarbons to give the corresponding olefinically unsaturated hydrocarbons, in particular for dehydrogenating ethylbenzene to give styrene.

Such catalysts and their preparation are described, for example, in U.S. Pat. No. 3,904,552 (1), the European Patents 177 832 (2), 181 999 (3), 195 252 (4), 296 285 (5), 297 685 (6), 297 657 (7) and 502 510 (8) and DE-A 28 15 812 (9), 28 15 874 (10), 36 43 382 (11) and 38 21 431 (12).

Apart from iron and potassium, the known catalysts generally contain promoters, ie. elements which, at least after the preparation process, are generally present in the form of their oxides. Promoters described are, for example, Mo, Ce (1), W (4), Mg (2, 3), V, Cr (9), Ti (8) and other elements. In the preparation process, these constituents are processed together with the iron and potassium compounds in the form of oxides or decomposable compounds to give pastes which contain the constituents of the future catalyst in the form of precursors and form oxides on subsequent heating (calcination). It is possible to add further auxiliaries, eg. organic compounds or graphite, which are burned on subsequent heating, for example to improve the shapability of the paste or to favorably influence the hardness and porosity of the finished catalyst.

After intimate mixing, for example dry mixing of the constituents or a spray-dried powder produced therefrom, if desired with addition of water, shaped bodies are produced which are then dried and calcined at from about 300 to 1100° C. and thus converted into the finished catlaysts (1, 4, 9). According to (12), a defined compound, viz. a potassium ferrite of the formula $K_2Fe_{22}O_{34}$, is also effective as catalyst.

Reference (5) discloses, in particular, a process having two calcination steps in which methylcellulose or graphite is added to the raw composition, these being burned out at from 250° C. to 600° C., after which, in a further step at from 700 to 800° C., the remaining carbonates too are converted into the corresponding oxides.

However, the known catalysts are still far removed from being able to give an ideal result, ie. they still form undesired byproducts and also appear to be capable of improvement in terms of the specific output (possible space-time yield) and their life under industrial conditions (mechanical stability).

It is an object of the present invention to provide a process by means of which it is possible to prepare catalysts of the type indicated in the introduction which are improved in terms of activity and selectivity and also the mechanical stability.

We have found that this object is achieved by the process of the present invention which gives catalysts having higher porosity, higher activity and better selectivity than the known catalysts.

It has been found that it is possible to prepare improved catalysts comprising iron and potassium and, if desired, further elements, which catalysts are suitable for dehydrogenating hydrocarbons, in particular for dehydrogenating ethylbenzene to give styrene, by preparing a finely divided, preferably aqueous, mixture of an iron compound with a potassium compound and, if desired, compounds of further elements, drying the mixture if appropriate, heating (calcining) it in a first step so that agglomerates having a diameter of from 5 to 50 μm and formed from smaller individual particles are obtained and, in a second step, preferably after shaping, heating (calcining) it at from 300 to 1000° C.

Iron, potassium and, if desired, promoters are mixed with one another in the form of oxides or of substances which are converted into oxides on heating.

As iron compound, preference is given to using $Fe_2O_3$ (haematite), FeOOH (goethite), $Fe_3O_4$ or another synthetic or naturally occurring oxidic iron compound.

As potassium compound, preference is given to using potassium carbonate, potassium hydroxide or another potassium compound such as potassium oxalate which can be decomposed by heat; it is also possible to use a potassium compound containing the intended promoter (ie. as corresponding anion or as double salt).

The iron and potassium compounds used can be, completely or in part, a potassium ferrite compound. As promoters, not only cerium but also, for example, at least one compound selected from among compounds of Al, Ca, Co, Cr, Cs, Li, Mg, Mo, Na, W, V or Zn can be added. Particular preference is given to compounds of Ca, Ce, Mg, Mo or W.

The mixing of the raw materials and the first drying should lead to very small particles which should have, for example, a diameter of from 0.1 to 10 μm.

Suitable methods of preparing such finely divided mixtures are known per se and comprise, for example, milling and/or grinding techniques; while household appliances such as mixers are quite suitable for laboratory experiments, kneaders, pan mills or ball mills are preferred for industrial purposes.

The intensive mixing of iron and potassium compounds forms, sometimes to a considerable extent, potassium-iron compounds such as potassium ferrites of different overall composition. These generally form crystallites of the dimensions mentioned, viz. 0.1 to 10 μm, and should merely sinter together during the subsequent calcination, but not disappear.

Finally, there is obtained a finely divided, dry or preferably aqueous mixture having, for example, a solids content of from 10 to 80%.

The drying of the aqueous mixture (spray slurry) prior to the first heating step is advantageously carried out by spray drying. In spite of the temperature of the drying air which can be, for example, from 300 to 600° C., the particles formed are generally not heated to a temperature higher than about 100° C., for a short time also up to 150° C., since the evaporating water prevents a higher temperature. The formation of sufficiently small particles is influenced by the way in which the spray device is operated. The spray device used is advantageously a rotating spray nozzle or a rotary disk whose speed of rotation can, depending on the solids content of the spray slurry, be, for example, from 10,000 to 30,000 $min^{-1}$. The most favorable speed of rotation is, depending on the solids content of the spray slurry, best determined by a preliminary experiment.

The spray-dried powder obtained should, according to the present invention, comprise agglomerates having a diameter of from about 5 to 50 μm, preferably from 15 to 35 μm, which are made up of the smaller particles originally present. The type of adhesion can be referred to as sintering or baking together. It is important that these agglomerates are not destroyed during subsequent heating (calcination) and also not during the subsequent shaping. The agglomerates are stabilized if the mixture is heated at from 600° C. to 1200° C. in the first step, with the duration of heating naturally also playing a role. It has been found to be advantageous to heat the material for a period of up to 24 hours in the first step.

It is particularly advantageous according to the present invention to apply the process to the preparation of a catalyst containing a cerium compound; it is to be particularly recommended to add the cerium compound completely or in part to the precalcined catalyst only after the first step and then to calcine again. It appears that this measure succeeds in increasing the effective surface area and thus improve the activity.

For this purpose, any missing cerium compound, any further promoters, also any further iron oxide and (further) auxiliaries are added to the precalcined composition, preferably mixed wet, and shaped bodies are produced from the mixture, these then being dried if appropriate and calcined again at from 300 to 1000° C. It is favorable according to the present invention to keep the temperature of the second calcination step, for example, in the range from 500 to 900° C., preferably not above 800° C., with the maximum calcination temperature in the second step generally being at least 30° lower than the calcination temperature in the first step. At temperatures significantly above from 800 to 900° C., depending on the duration of heating, larger crystallites are formed in the case of catalysts containing cerium, which is not desired.

Shaped bodies produced are, for example, pellets or extrudates, but other shaped bodies are also possible, depending on the process in which it is intended to use the catalyst, since such a process is generally designed for the use of particular shapes and dimensions of the catalyst.

The process of the present invention enables the porosity and the internal surface area of the catalysts to be increased without the mechanical stability suffering.

The preparative process of the present invention also achieves, inter alia, formation of smaller crystallites from the incorporated cerium or its compounds, which is accompanied by an increase in the effective surface area. This improves both the activity and the selectivity of the catalysts in dehydrogenation reactions.

PREPARATIVE EXAMPLE

A spray-dried powder was prepared from 100 g of FeOOH and 12 g of $K_2CO_3$ and was calcined for 24 hours at 900° C. After calcination, 7.5 g of $K_2CO_3$, 4.2 g of $CaCO_3$, 4.4 g of $WO_3$ and 12.8 g of $Ce_2(CO_3)_3$ were added and, after suspension in water, the mixture was again spray dried. An extrudable composition was then prepared by adding water and kneading and was extruded. After drying and heating, the extrudates were calcined at 700, 800 and 900° C. (according to the present invention; catalysts 25 to 27).

Testing of Performance

The catalysts are tested in an experimental apparatus replicating the industrially operated isothermal process. For this purpose, 407 cm³ of solid catalyst extrudates are placed in a reaction tube having an internal diameter of 30 mm. First, 268 g/h of ethylbenzene and 536 g/h of water vapor are passed over the catalyst for 10 days, with the temperature being selected in such a way that a conversion of 70% is established. The feed is then changed to 300 g/h of ethylbenzene and 418 g/h of water. The temperature is set to 590° C. for 3 days and after 3 days the conversion, selectivity and composition of the reaction mixture is determined by analyzing the reaction products (liquid and off-gas).

TABLE

| | Catalytic properties | | | | | | | | |
|---|---|---|---|---|---|---|---|---|---|
| No. | 2 | 5 | 8 | 11 | 14 | 17 | 20 | 23 | 25 |
| Conversion | 39.3 | 42.0 | 44.2 | 45.40 | 45.6 | 43.8 | 42.6 | 45.2 | 44.1 |
| Selectivity | 97.9 | 97.8 | 98.0 | 97.7 | 97.9 | 98.1 | 98.0 | 98.0 | 98.1 |

Comparison of the physical properties of the catalysts 4 to 27 according to the present invention with the comparative samples 1 to 3 shows that the porosity and the BET surface area were able to be greatly increased. The effectiveness comparison (table) shows that activity and selectivity have been greatly improved. Compared with the Comparative Catalyst 2 prepared by the process hitherto customary, catalyst 25, for example, shows a simultaneous improvement in activity and selectivity over the entire conversion range.

We claim:

1. A process for preparing catalysts comprising iron and potassium, which catalysts are suitable for dehydrogenating hydrocarbons to give the corresponding olefinically unsaturated hydrocarbons, wherein a finely divided dry or aqueous mixture comprising an iron compound and a potassium compound is prepared, the mixture, if it is aqueous, is dried, heated in a first step so that agglomerates having a diameter of from 5 to 50 μm and formed from smaller individual particles are obtained and, in a second step, after shaping, heated at from 300 to 1000° C.

2. A process as defined in claim 1, wherein an aqueous mixture having a solids content of from 10 to 80 percent by weight is prepared and spray dried.

3. A spray-dried mixture prepared by the process as defined in claim 2 and having an internal surface area, determined by the BET method, of at least 3 m²/g.

4. A process as defined in claim 1, wherein the mixture is heated at from 600° C. to 1200° C. in the first step.

5. A process as defined in claim 1, further comprising addition of cerium.

6. A process as defined in claim 1, wherein a cerium compound is added after the first heating and before the second heating.

7. A process as defined in claim 1, wherein the maximum temperature in the second step is at least 30° lower than the temperature in the first step.

8. A process as defined in claim 1, wherein the temperature of the second step is in the range from 500 to 800° C.

9. A process as defined in claim 1, wherein the iron compound is an iron oxide.

10. A process as defined in claim 1, wherein the iron compound is $Fe_2O_3$, FeOOH or $Fe_3O_4$.

11. A process as defined in claim 1, wherein the potassium compound is $K_2CO_3$, KOH or a potassium compound which can be decomposed by heat to give an oxide.

12. A process as defined in claim 1, wherein the iron and potassium compounds are, completely or in part, a potassium ferrite compound.

13. A process as defined in claim 1, further comprising addition of at least one compound selected from among compounds of Al, Ca, Ce, Co, Cr, Cs, Li, Mg, Mo, Na, W, V or Zn.

14. A process as defined in claim 13, further comprising addition of a compound selected from among compounds of Ca, Ce, Mg, Mo or W.

15. A process for dehydrogenating alkylaromatic or aliphatic hydrocarbons to give the corresponding alkenes, comprising contacting the hydrocarbons with a catalyst obtained by the process of claim 1.

16. A process as defined in claim 15, wherein the hydrocarbon is ethylbenzene and is dehydrogenated to give styrene.

* * * * *